United States Patent [19]
Cavallini

[11] Patent Number: 5,707,999
[45] Date of Patent: Jan. 13, 1998

[54] USE OF ALFUZOSIN OR TERAZOSIN IN THE TREATMENT OF PREMATURE EJACULATION

[75] Inventor: Giorgio Cavallini, Ferrara, Italy

[73] Assignee: Synthelabo, Le Plessis-Robinson, France

[21] Appl. No.: 624,603

[22] PCT Filed: Nov. 8, 1994

[86] PCT No.: PCT/EP94/03661

§ 371 Date: Apr. 16, 1996

§ 102(e) Date: Apr. 16, 1996

[87] PCT Pub. No.: WO95/13072

PCT Pub. Date: May 18, 1995

[30] Foreign Application Priority Data

Nov. 12, 1993 [IT] Italy ................... MI93A2412

[51] Int. Cl.$^6$ ................... A61K 31/505
[52] U.S. Cl. ................... 514/260
[58] Field of Search ................... 514/260

[56] References Cited

FOREIGN PATENT DOCUMENTS

92/11851 7/1992 WIPO.

OTHER PUBLICATIONS

Medical Science Research, vol. 20, No. 4, 1992, pp. 133–135, "The Effect of Terazosin, A Selective Alpha–Adrenoceptor Antagonist, on the Fertility of Male Rats" by W.D. Ratnasooriya et al.

ACTA Europaea Fertilitatis, vol. 17, No. 1, 1986, pp. 43–45, "Effect of an Alpha–Blocking Agent (Phenoxybenzamine) in the Management of Premature Ejaculation" by G. Beretta et al.

Fertility and Sterility, vol. 42, No. 4, 1984, pp. 659–661, "The Use of Phenoxybenzamine Treatment in Premature Ejaculation" by M. Shilon et al.

Contraception, vol. 41, No. 4, 1990, pp. 441–447, "Impairment of Fertility of Male Rats with Prazosin" by W.D. Ratnasooriya et al.

Neuroendocrinology, vol. 41, No. 1, 1985, pp. 36–43, "Evidence for the Modulation of Sexual Behaviour by Alpha–Adrenoreceptors in Male Rats" by J.T. Clark et al.

Life Sciences, vol. 45, No. 14, 1989, pp. 1263–1270, "The Role of the 5–HT2 Receptor in the Regulation or Sexual Performance of Male Rats" by M.M. Foreman et al.

The Merck Index, 1989, Merck & Co., Inc., Rahway, NJ, USA, pp. 40–41 and pp. 1441–1442.

The Urologic Clinics of North America, vol. 21, No. 3, Aug. 1994, pp. 365–376, "Prevention of Male Infertility: An Update" by S.T. Thompson et al.

*Primary Examiner*—Rebecca Cook
*Attorney, Agent, or Firm*—Griffin, Butler, Whisenhunt & Kurtossy

[57] ABSTRACT

The method of use of the α-1 blockers, alfuzosine and terazosine, in the treatment of premature ejaculation is disclosed.

4 Claims, No Drawings

USE OF ALFUZOSIN OR TERAZOSIN IN THE TREATMENT OF PREMATURE EJACULATION

This is a 371 of PCT/EP94/03661 filed Nov. 8, 1994.

The present invention relates to the use of α1 blockers in the treatment of premature ejaculation.

BACKGROUND OF THE INVENTION

Primitive psychogenic premature ejaculation is regarded as the most common sexual disorder of the male.

At present, the treatment of choice is psychotherapy, either as a behavioural dual team sex therapy according to Master & Johnson protocol, or individual psychotherapy (Rifelli and Moro. Sessuologia Clinica. Bologna, 1989). The first proved to be active in about 80% of the cases, and it needs an active couple with a strong background of conjugal life free from conflictualities, while the second proved to be active in 40%–60% of the cases. This means that a large amount of males do not benefit from the psychotherapy and still suffer from premature ejaculation.

Ejaculation is a centrally, integrated peripheral evoked reflex, which occurs as a result of α1-adrenergic receptor activation.

Effective pharmacological drugs for the treatment of premature ejaculation exist, but they suffer from severe side effects, for example clomipramine and phenoxybenzamine. Other treatments have a limited effectiveness (metoclopramide and the like).

SUMMARY OF THE INVENTION

Now it has been found that two specific α1-blockers, alfuzosine and terazosine, are effective in the treatment of psychogenic premature ejaculation. Particularly, said drugs turned out to be effective in patients who proved to have no benefit from psychological therapy.

Therefore, it is an object of the present invention to use alfuzosine and terazosine and the pharmaceutically acceptable salts thereof for the preparation of a medicament useful for the treatment of psychogenic premature ejaculation.

DESCRIPTION OF PREFERRED EMBODIMENTS

Alfuzosine and terazosine are a1 blockers used in the treatment of hypertension or in the symptomatic treatment of benign prostatic hyperplasia. Up to now no reference appears in literature about any possible use thereof in the treatment of psychogenic premature. ejaculation, particularly in patients resistant to psychotherapy.

In the following, the clinical evaluation of alfuzosine and terazosine is illustrated.

107 Patients complaining of psychogenic premature ejaculation were tested during 2 years. Age range was 21–63 years, mean age 34.3 years: all of them were put into a blind cross-over prospective controlled trial.

Alfuzosine, terazosine and placebo (vitamin C) were used.

Criteria for the participation in the study were absence of: uncontrolled hypertension, orthostatic hypotension, thyroid diseases, uncontrolled diabetes, recent miocardial infarction, use of alfuzosine or of terazosine in the previous 4 months, sexual life characterised by occasional intercourses.

The patients were randomized in three groups: two of 36 and one of 35 patients. Each group used alfuzosine, terazosine or placebo in a different order. The first group used the drugs as follows: alfuzosine, terazosine, placebo; the second group used first terazosine, followed by placebo and alfuzosine; the third group used first placebo, then alfuzosine and finally terazosine. Each drug was used during two months. Alfuzosine dosage was 2 mg three times per day, terazosine 5 mg once a day (the dosage was gradually reached starting from 1 mg/day) and vitamin C 500 mg two times per day.

Six patients dropped out from the study for unknown causes, and 4 patients had to be discharged from the study due to the side effects of the drugs.

At the end of each two-month period of treatment, the patients and their partners were separately asked whether or not they were satisfacted by the activity of the drugs: i.e. whether or not time required to reach ejaculation had been prolonged enough to be satisfactory for both. In 6 cases a disagreement about the times of orgasmic latency was evidenced between patients and their partners and therefore these were discharged from the study.

At the end of the study, 91 cases were evaluated, which were subdivided into a first group of 30 patients, a second of 30 and a third of 31. Results were categorized as follows: positive (satisfactory for both partners) or negattve (unsatisfactory for both partners). Data were analyzed with the chi square test.

The results are listed in the following tables.

Table 1 shows the activity of the drugs: alfuzosine proved to be active in 42 patients (46.2%), terazosine in 48 (53,7%) and placebo in 22 (24.2%).

TABLE 1

Effect of α1-blockers in the treatment of premature psychogenic ejaculation

| Group I | alfuzosine | terazosine | placebo |
| --- | --- | --- | --- |
| positive results | 14 (46.7%) | 16 (53.3%) | 8 (26.7%) |
| negative results | 16 (53.3%) | 14 (46.7%) | 22 (73.3%) |
| TOTAL | 30 | 30 | 30 |

| Group II | terazosine | placebo | alfuzosine |
| --- | --- | --- | --- |
| positive results | 15 (50.0%) | 10 (33.3%) | 13 (43.3%) |
| negative results | 15 (50.0%) | 20 (66.7%) | 17 (56.7%) |
| TOTAL | 30 | 30 | 30 |

| Group III | placebo | alfuzosine | terazosine |
| --- | --- | --- | --- |
| positive results | 4 (12.9%) | 16 (51.6%) | 17 (54.8%) |
| negative results | 27 (87.1%) | 15 (48.4%) | 14 (45.2%) |
| TOTAL | 31 | 31 | 31 |

The results prove that alfuzosine and terazosine are significantly more active than placebo (chi square 8.70, p<0.05 and 14.50, p<0.01 respectively) whereas non significant differences were evidenced between alfuzosine and terazosine (chi square 0.55, p not significant). When placebo was used as. first (III group), this turned out to be active for 12.9% of cases,; on the other hand, when used after the α-blocker, it proved effective in about 30% of cases, a trend which, even though suggestive, is not significant (chi square 2.55).

Table 2 shows side-effects. The 4 patients who had been discharged from the clinical evaluation were also considered.

TABLE 2

Side effects induced by the treatment with alfuzosine, terazosine and placebo.

|  | Appearance of side effects | No side effects |
| --- | --- | --- |
| Alfuzosine | 5^ (5.2%) | 90 (94.8%) |
| Terazosine | 3* (3.2%) | 90 (96.7%) |
| Placebo | 1+ (1.1%) | 90 (98.9%) |

^ 3 patients reported hypotension (2 patients of group 1 interrupted the treatment and received no terazosine), 1 hypotension and epigastralgia, 1 epigastralgia.
* 2 patients of group 2 reported hypotension, interrupted the treatment and received no placebo, 1 reported headache.
+ 1 patient reported slight epigastralgia.

The results of clinical evaluation prove that α1-blockers alfuzosine and terazosine are effective in the treatment of psychogenic premature ejaculation, particularly in patients resistant to psychotherapy. The use of said drugs proved to be safe from the side effects point of view.

The dosage will be determined by the physician depending on the severity of the pathology and the general conditions of the patient.

Generally, dosages from 1 to 8 mg/day for alfuzosine and from 3 to 15 mg/day for terazosine can be envisaged, possibly subdivided into more daily doses.

According to another object of the invention, alfuzosine and terazosine can also be used in combination in the same medicament, or in combination with one or more compounds effective in the treatment of premature ejaculation, such as antiandrogens, metoclopramide, clomipramine, phenoxybenzamine, prazosine and lorazepam.

The preferred administration route is the oral one, but other administration routes can also be envisaged.

According to the invention, the drugs herein described will be administered in form of pharmaceutical compositions. which can be prepared according to conventional procedures, for example as described in Remington's Pharmaceutical Sciences Handbook, XVII ed, Mack, Pub., USA.

Examples of pharmaceutical compositions are tablets, capsules sugar-coated pills, syrups, chewable formulations; suppositories and injectable formulations (intravenous, subcutaneous, intramuscular).

I claim:

1. A method for treatment of psychogenic premature ejaculation comprising administering to a patient suffering from psychogenic premature ejaculation an effective amount of alfuzosine or a pharmaceutically acceptable salt thereof.

2. The method of claim 1, wherein the dosage administered to the patient is from 1 to 8 mg/day.

3. The method of claim 1, wherein the administration is by oral administration.

4. The method of claim 1, wherein the alfuzosine is administered in a composition selected from the group consisting of a tablet, capsule, pill, syrup, chewable formulation, suppository. and injectable formulation.

* * * * *